(12) United States Patent
Holmes (10) Patent No.: US 7,153,281 B2
(45) Date of Patent: Dec. 26, 2006

(54) APPARATUS AND METHOD FOR MEASURING INSTABILITY OF A MOTION SEGMENT UNIT OF A SPINE

(75) Inventor: David C. Holmes, Miami, FL (US)

(73) Assignee: Mekanika, Inc, Boca Raton, FL (US)

( * ) Notice: Subject to any disclaimer, the term of this patent is extended or adjusted under 35 U.S.C. 154(b) by 311 days.

(21) Appl. No.: 10/697,852

(22) Filed: Oct. 30, 2003

(65) Prior Publication Data

US 2004/0116835 A1 Jun. 17, 2004

(51) Int. Cl.
*A61B 5/00* (2006.01)
(52) U.S. Cl. ..................................... 600/594
(58) Field of Classification Search ............... 600/594, 600/595, 587
See application file for complete search history.

(56) References Cited

U.S. PATENT DOCUMENTS

| | | | | |
|---|---|---|---|---|
| 3,750,652 A | * | 8/1973 | Sherwin | 606/90 |
| 4,899,761 A | * | 2/1990 | Brown et al. | 600/594 |
| 5,059,194 A | * | 10/1991 | Michelson | 606/61 |
| 5,308,357 A | * | 5/1994 | Lichtman | 606/205 |
| 5,776,054 A | | 7/1998 | Bobra | |
| 5,899,901 A | * | 5/1999 | Middleton | 606/61 |
| 5,935,151 A | | 8/1999 | Broughton et al. | |
| 6,716,218 B1 | * | 4/2004 | Holmes et al. | 606/105 |

* cited by examiner

*Primary Examiner*—Max Hindenburg
(74) *Attorney, Agent, or Firm*—Watov & Kipnes, P.C.

(57) ABSTRACT

Apparatus and method for measuring spinal instability through the use of a distractor arm assembly having segments pivotal with respect to each other and movable through the movement of a pivotal collar assembly along a centrally positioned jackscrew.

19 Claims, 9 Drawing Sheets

APPARATUS AND METHOD FOR MEASURING INSTABILITY OF A MOTION SEGMENT UNIT OF A SPINE

FIELD OF THE INVENTION

The present invention is generally directed to an apparatus and method for measuring instability of a motion segment unit of a spine in which at least two force applying members are attached in spaced apart locations to the motion segment unit and a force applied thereto to assist a surgeon in selecting a suitable course of treatment to correct or improve the instability of the motion segment unit.

BACKGROUND OF THE INVENTION

It is well known that back pain is one of the most frequently occurring and expensive disabling ailments, especially for patients in the 30–60 year age bracket. Although back pain syndrome is a very common occurrence, its diagnosis to this day is very difficult.

The vertebral column (spine) is a biomechanical structure composed primarily of ligaments, muscles, vertebrae and intervertebrae discs. The biomechanical functions of the spine include (1) support of the body (trunk and appendages), which involves the transfer of the weight and the bending moments of the head, trunk and arms to the pelvis and legs, (2) complex physiologic motion between these body parts, and (3) protection of the spinal cord and nerve roots.

The major regions of the spine are the cervical, thoracic, lumbar and sacral. The vertebrae increase in size and mass from the cervical to the lumbar regions. The increase in size of the vertebrae is directly related to an increased capacity for supporting larger loads. The lumbar region is therefore the major load bearer of the spine. However, this increase in load bearing capacity is paralleled by a decrease in flexibility. Because the lumbar regions bears heavier loads than other regions of the spine, the lumbar trunk (low back structure) is more, but not exclusively, susceptible to strain and hence back pain.

The spine is comprised of different levels known as motion segment units. The lumbar spine, for example, is comprised of five motion segment units. The motion segment unit is the smallest component of the spine that exhibits kinematic behavior similar to that of the whole spine. The motion segment unit is capable of flexion, extension, lateral bending, torsion and translation. The components of each motion segment unit include two adjacent vertebrae and their apophyseal joints, the intervertebral disc and the connecting ligamentous tissue.

Many causes of back pain and related neurological pain, are attributed to the instability of the motion segment unit. Segmental instability is defined as "the loss of ability of the spine under physiologic loads to maintain relationships between vertebrae in such a way that there is neither damage nor subsequent irritation to the spinal cord or nerve roots, and, in addition, there is no development of incapacitating deformity or pain due to structural changes". Instability is therefore an abnormal response to applied loads characterized by motion in the motion segment unit beyond normal constraints. Excess motion can be abnormal in quality (i.e., abnormal coupling patterns) or in quantity (abnormal increased motion) or both. Excess motion may well result in damage to the nerve roots, the spinal cord, and other spinal structures.

The underlying causes of the structural changes in the motion segment unit leading to instability are trauma, degeneration, aging, disease (tumor, infection, etc.), surgery, or a combination thereof. It is known that a mechanically unstable motion segment unit can originate due to loss of biomechanical function of the spine joint ligaments and degeneration of the intervertebral disc and nucleus pulposus. A degenerate nucleus polposus causes disc space narrowing, loss of viscoelastic properties and the subsequent transfer of compressive loads to the annulus fibrosus. The altered anatomic dimensions and subsequent abnormal response to loading can cause loss of pretension in the ligamenum flavum, and longitudinal ligaments, degeneration of the facet capsules (and possible subluxation) with a consequence of secondary degenerative osteoarthritis of the joints.

Spinal disorders requiring neural decompressive surgery can leave motion segment units unstable due to the removal of supporting structures of the joint. A severely unstable motion segment unit is most likely to be fused to insure postsurgical stability. The need to fuse the vertebrae of a motion segment unit is dependent on the pre-operative symptoms and clinical (radiographic) findings and on the outcome of the surgical procedure.

One effort at mechanically determining spinal instability is disclosed in "A Technique for Mechanical Assessment of the Intervertebral Joint", Mark Lubin et al., Biomech. Sym. ADM vol. 43 (1981). A Cloward lamina spreader is fitted with a strain gauge and a loading and unloading of force is provided manually. The device disclosed in the aforementioned publication is disadvantageous because there is no recognition of the need to control the rate of displacement nor a means for doing so which enables precise measurements of relative stiffness of the motion segment unit. The motion segment unit is a viscoelastic structure and therefore its resistance to deformation is dependent on the loading rate. Objective criteria for determining the degree of instability of the motion segment unit is therefore important in assessing whether spinal fusion surgery is necessary to relieve back pain in the patient.

Figure 2:
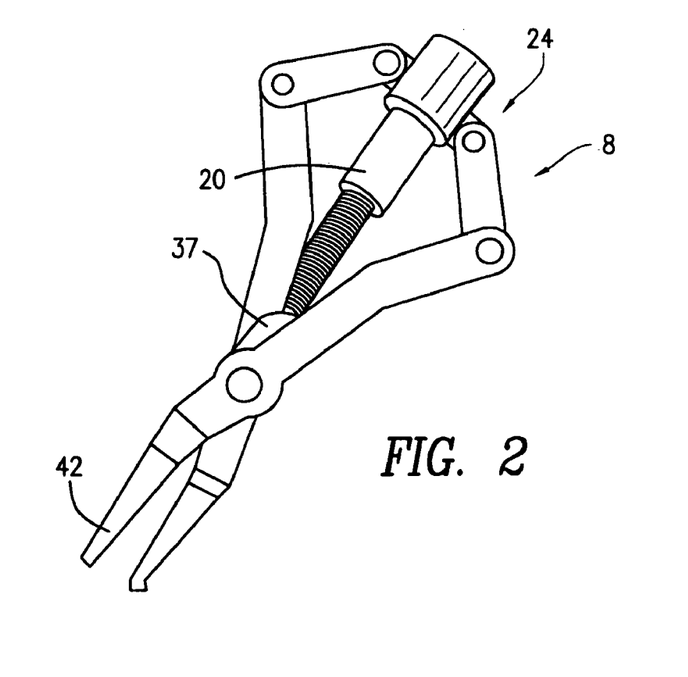
FIG. 2 is a perspective view of a further embodiment of a distractor arm assembly with two distractor arms in accordance with the present invention.

Another effort at measuring the relative instability of the motion segment unit of the spine is disclosed in Mark D. Brown and David C. Holmes (U.S. Pat. No. 4,899,761). The apparatus disclosed in this reference provides a vertebrae distractor including a device for applying a constant rate of increasing force against adjacent vertebrae of a motion segment unit to thereby distract or separate the vertebrae. Means for detecting and recording the changes in the resistance to distraction are also provided. The device disclosed in the '761 Patent, while providing useful objective criteria regarding the relative stiffness of a motion segment unit of the spine, nonetheless, requires the removal of spinal tissue in order to place the distractor legs in a suitable position for operating the device as shown in FIG. 2 of the reference. In particular, it is often necessary to remove the interspinous ligaments from adjacent vertebrae in order to provide placement of the distractor device in an operable position to measure spinal stiffness. The removal of spinal tissue with this procedure may contribute to the instability of the motion segment unit. Thus, the surgeon must first further destabilize the motion segment unit before a measurement can be taken and this may have a bearing on the type of implantable spinal assist device that may be used to correct the instability and the degree to which the patient may recover from the spinal surgery.

It would therefore be a distinct advantage in the art for measuring and treating instability of a motion segment unit of the spine if a device used to determine the relative stiffness of a motion segment unit did not result in significant damage and/or removal of spinal tissue in order to make the appropriate measurements of spinal stiffness.

It would be a further advantage in the art to provide a device for measuring spinal instability which can be readily attached to preselected positions of the motion segment unit during operation without significant tissue damage.

It would be a still further advantage in the art to provide a device for measuring spinal instability which can be employed in a comprehensive system in which spinal stiffness or other characteristics of the motion segment unit can be matched with a suitable spinal assist device such as a spinal implant device for reducing or eliminating instability of the motion segment unit.

SUMMARY OF THE INVENTION

In accordance with the present invention, there is provided an apparatus and method for measuring instability of a motion segment unit of the spine in which significant damage and/or removal of spinal tissue is reduced or eliminated during the process of making measurements of the relative stiffness of the spine. The apparatus and method may be effectively employed in a comprehensive system of associating a measured characteristic of the motion segment unit (e.g. stiffness) which an appropriate spinal assist device (e.g. a spinal implant device) to reduce or eliminate the instability of the affected motion segment unit.

In one aspect of the present invention, there is provided an apparatus and method for measuring instability of a motion segment unit of a spine comprising:
a) motor means for applying a controllable force to a distractor arm assembly;
b) a distractor arm assembly operatively engaged to the motor means comprising:
  1) a collar assembly fixedly secured to the motor means,
  2) screw means operatively engaged to the motor means through said collar assembly, and rotatable when the motor means is operational, and
  3) a pair of arms each having at least two arm segments pivotal with respect to each other, a first of said arm segments being attached to the collar assembly and a second arm segment having a remote end for engaging a portion of the motion segment unit of the spine, and
  4) a pivot collar assembly for engaging the second arm segments enabling the second arm segments to be movable with respect to each other, wherein rotation of the screw means causes the pivot collar assembly to move causing the first and second arm segments to move relative to each other whereby the remote ends of the arms move away from each other to provide a controllable force on adjacent portions of a motion segment unit and toward each other to release the controllable force against said adjacent portions of the motion segment unit.

The controllable force or load generated by the motor means and applied through the distractor arm assembly may be a force sufficient to provide a constant rate of distraction on the motion segment unit or may be a constant rate of force resulting in a particular displacement profile of the motion segment unit. In either application the resulting force or displacement readings can be associated with a characteristic of the motion segment unit (e.g. stiffness) facilitating the adaptation by the surgeon of a suitable course of treatment.

In a further aspect of the present invention, there is provided an apparatus and method for measuring instability of a motion segment unit of a spine comprising:
c) motor means for applying a controllable force to a distractor arm assembly;
d) a distractor arm assembly operatively engaged to the motor means comprising:
  1) a collar assembly fixedly secured to the motor means,
  2) screw means operatively engaged to the motor means through said collar assembly and rotatable when the motor means is operational,
  3) a pair of arms each having at least two arm segments pivotal with respect to each other, a first of said arm segments being attached to the collar assembly and a second arm segment having a remote end in the form of a dual leg assembly for engaging of the motion segment unit of the spine, and
  4) a pivot collar assembly for engaging the second arm segments enabling the second arm segments to be movable with respect to each other.

wherein rotation of the screw means causes the pivot collar assembly to move causing the first and second arm segments to move relative to each other whereby the dual leg assembly exerts a controllable force on adjacent portions of a motion segment unit.

In a further aspect of the invention, the apparatus is adapted to engage a spine imbedded attachment device within a preselected portion of the motion segment unit and through the attachment device the constant rate of force is exerted against respective portions of the motion segment unit.

In a further aspect of the invention there is provided a detection means connected to the distractor arm assembly for measuring the resistance of the pair of arms to said distraction which is related to the resistance of the adjacent vertebrae of the motion segment unit to said distraction, at a plurality of force exerting positions, said detection means generating an output signal corresponding to said resistance. There may be further provided translation means adapted to receive the output signal for the detection means and for translating the output signal into interpretable data such as a stiffness value.

BRIEF DESCRIPTION OF THE DRAWINGS

The following drawings in which like reference characters indicate like parts are illustrative of embodiments of the present invention and are not intended to limit the invention as encompassed by the application including the claims appended hereto.

DETAILED DESCRIPTION OF THE INVENTION

Referring the drawings and first to the embodiment of the invention shown in FIGS. 1–6, there is shown an apparatus 2 of the present invention which includes a stepper motor assembly 4 (See FIG. 4) which is capable of applying force preferably at a constant rate to a distractor arm assembly 8 as hereinafter described. On example of a stepper motor assembly 4 is described in U.S. Pat. No. 4,899,761 incorporated herein by reference. The stepper motor assembly 4 is contained within a housing 6. The apparatus also includes a distractor arm assembly 8 which, as described in detail hereinafter, is able to apply a constant force to spaced apart locations of a motion segment unit to separate and/or distract, and/or torque the same and thereby to enable the determination of reliable data on a characteristic (e.g. relative stiffness) of the motion segment unit.

Figure 1:
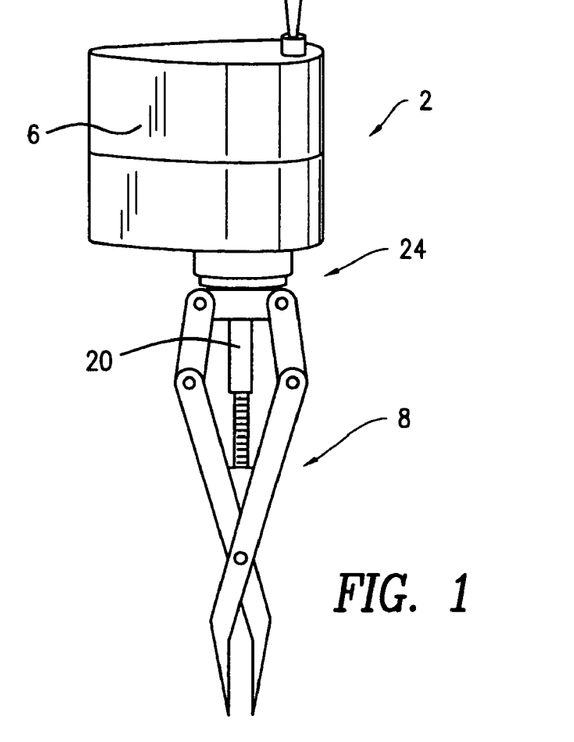
FIG. 1 is a side view of a first embodiment of the apparatus of the present invention including a distractor arm assembly including two distractor arms for placement between adjacent vertebrae of a motion segment unit and a motor assembly for operating the distractor arm assembly contained with a housing.
Figure 5:
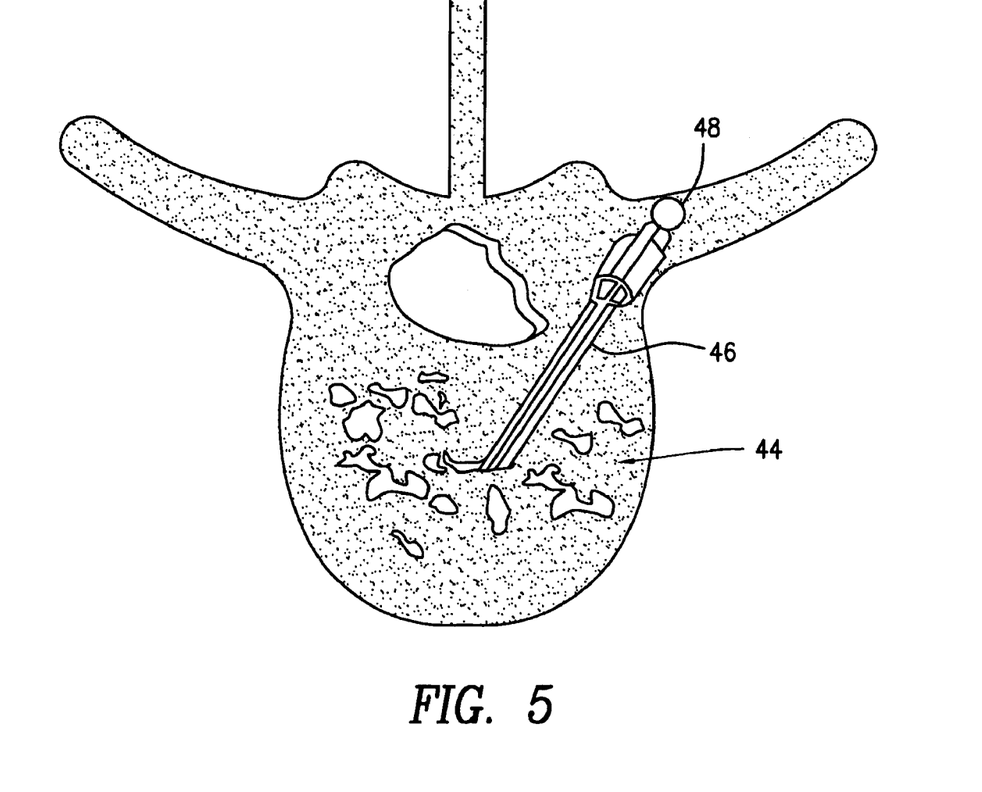
FIG. 5 is a cross-sectional view of a lumbar vertebrae showing a pedicle screw inserted therein wherein the pedicle screw is engageable by the distractor arm assembly of the present invention.

Referring specifically to FIGS. 1, 2 and 5, the housing 6 contains a stepper motor assembly 4 which includes a stepper motor 10 which provides rotational movement through a drive gear 12 and an idler gear 14.

Rotational movement is provided through an assembly including a coupler 18 which secures a jackscrew 20 therein. A series of ball bearings 22 secures the remote end of the jackscrew in the motor housing 6. There is also provided a load cell or strain gauge 16 for measuring resistance to the force applied by the distractor arm assembly 8.

A collar assembly 24 is operably connected to a lower portion of the housing 6. The collar assembly 24 is secured to the housing 6 through a port 26. An opening 28 is provided within the collar assembly 24 to allow the jackscrew 20 to pass therethrough into the housing 6.

Attached to the collar assembly 24 is the distractor arm assembly 8 which in accordance with the present invention includes two segmented distractor arms 32a and 32b. Each distractor arm 32a, 32b is provided with first arm segments 34a and 34b, and second arm segments 36a and 36b, respectively. The distractor arm assembly 8 may be released from the collar assembly 24 by operation of a release assembly 60 which can be a projection 62 reversibly securable within a slot 64 or by any other suitable means.

The first segments 34a and 34b are operably and rotatably connected to the collar assembly 24 through a connecting device 38a and 38b such as a screw, bolt or the like. The first segments 34 are operatively and rotatably connected to the second segments 36 through a similar type of connecting device 40a and 40b.

Figure 4:
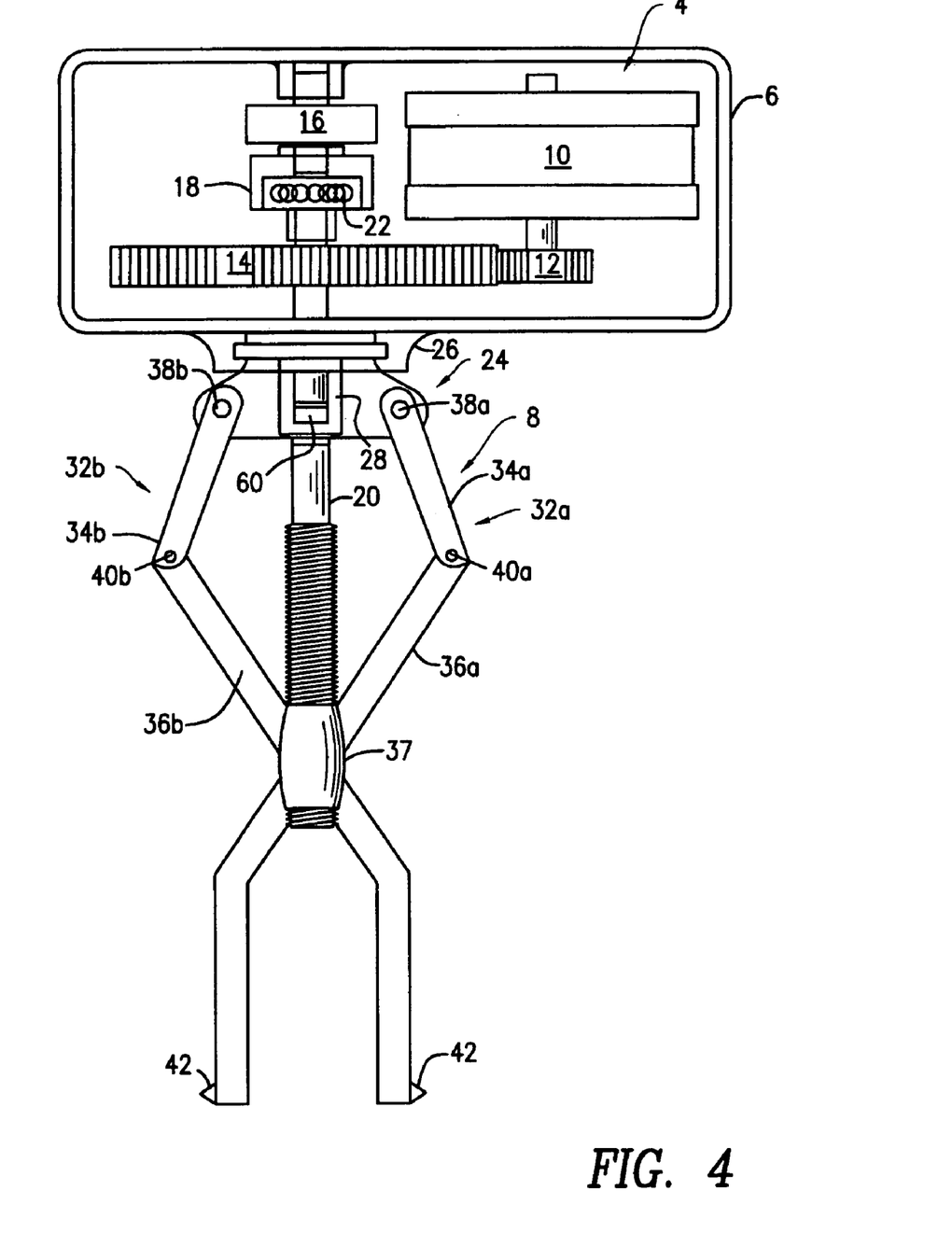
FIG. 4 is a cross-sectional view of the embodiment of the apparatus of the present invention shown in FIG. 1.

As shown in FIGS. 2 and 4, the second segments 36a and 36b are linked to the jackscrew 20 through a pivot collar assembly 37. As a result, the .second segments 36a and 36b are able to rotate with respect to each other thereby enabling the remote ends of the second segments to move toward and away from each other as described hereinafter.

Figure 3:
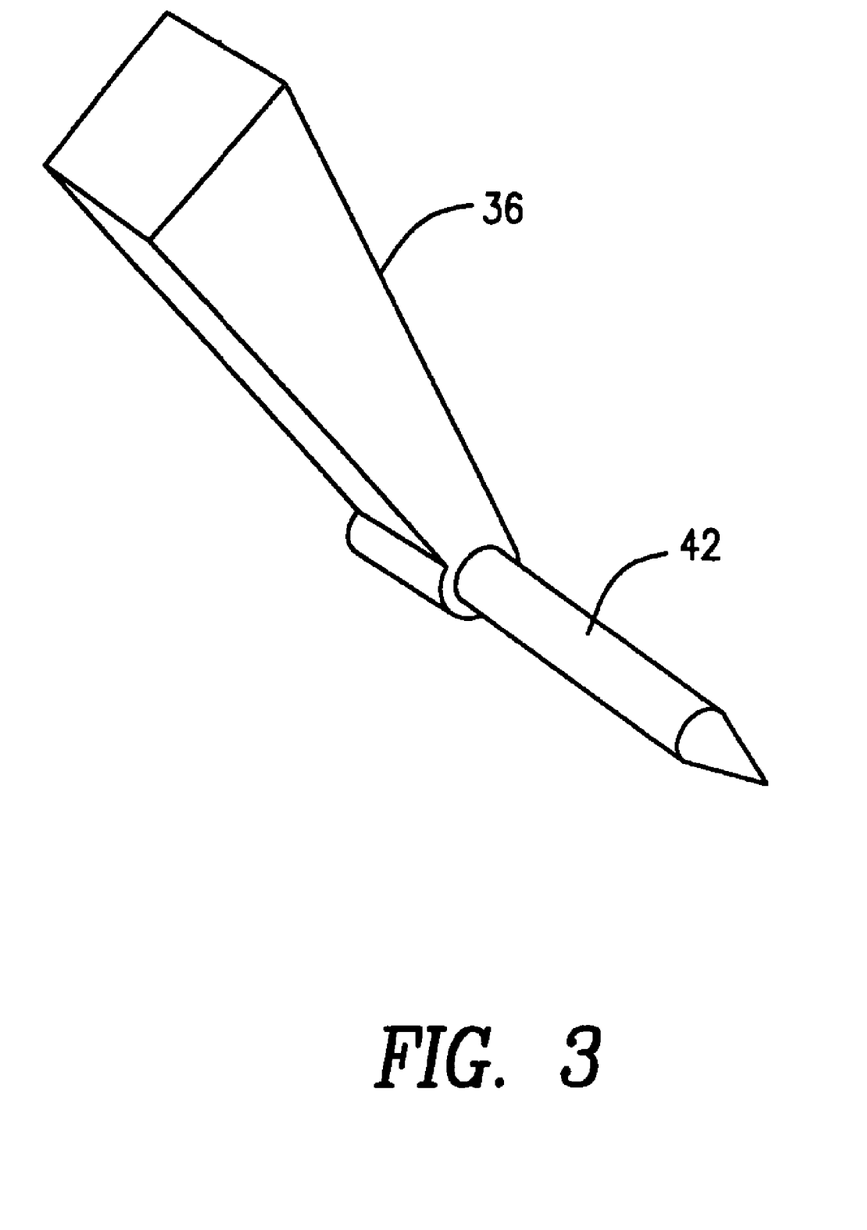
FIG. 3 is a perspective view of a portion of a distractor arm employing reusable or disposable pins for contacting the motion segment unit.

At the remote end of the second segments 36a and 36b, there is provided motion segment unit engaging devices which engage a portion of the motion segment unit of the spine. As shown in FIGS. 2–4, there is provided a pair of motion segment unit engaging devices in the form of pins 42 which are adapted to engage opposed portions of motion segment units as the second segments 36a and 36b move away from each other to thereby force apart the adjacent portions of the motion segment units as hereinafter described. The pins 42 which may be reusable or disposable may be any shape so long as the pin ends can engage the motion segment unit. It is desirable for the pins 42 to have a relatively small contact surface that engages the motion segment unit. It is also preferred that the pins are adjacent each other when placed in proximity to the motion segment unit to minimize damage to adjacent tissue. In addition to pins, pedicle screws and bone drill bits and similar devices may be used.

Figure 6:
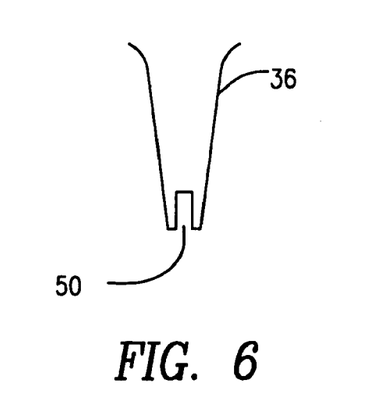
FIG. 6 is a schematic view of a portion of an arm of a distractor assembly adapted to engage a pedicle screw of the type shown in FIG. 5.

In an alternative embodiment as shown in FIGS. 5 and 6, the motion segment unit of a spine shown generally by the numeral 44 in FIG. 5 may be provided with a pin, pedicle screw, bone drill bit, or the like shown generally by the numeral 46 which is preinserted into the motion segment unit and has a head portion 48 which is adapted to be engaged by the remote end of the second segment 36 of the distractor arm 32. In particular and referring to FIG. 6, the remote end of the second segment 36 may be provided with a cavity 50 having a shape complimentary to the head portion 48 of the pin 46 so that the head portion 48 may be inserted into the cavity 50 to provide reversible locking engagement with the second segment 36 of the distractor arm 32.

Movement of the distractor arm assembly 8 is provided in the following manner. The stepper motor assembly 4 provides rotational movement to the jackscrew 20 through the drive gear 12 and idler gear 14. The jackscrew 20 is secured to the stepper motor assembly 4 through the employment of the coupler 18 and ball bearings 22. Rotational movement of the stepper motor causes the jackscrew 20 to rotate and thereby enable the pivot collar assembly 37 to move upwardly along the jackscrew 20 towards the stepper motor assembly 4. As the pivot collar assembly 37 moves upwardly, the first segments 34a and 34b move away from each other thereby causing a similar movement in the second segments 36a and 36b thereby causing the remote end of the second segments 36 to move away from each other and thereby move the respective portions of the motion segment unit away from each other. As a result, a measurable and preferable constant rate of distraction (displacement control) is applied, or a constant rate of force (force control), is applied against the motion segment unit and the resulting force, or displacement, can be associated with a rating of a characteristic of the motion segment (e.g. stiffness) which can assist the surgeon in deciding on an appropriate course of treatment including the implantation of spinal assist devices. Depending on the direction of rotation of the jackscrew 20, the segments may move toward each other thereby measuring the compressive stiffness of the motion segment unit.

For example, a method of measuring the relative stiffness of a motion segment unit is disclosed in U.S. patent application Ser. No. 10/683,505 filed on Oct. 10, 2003 (Attorney docket No. 508.1.014), incorporated herein by reference. The method includes applying a force against at least one pair of "targeted" adjacent vertebrae of the patient. The application of force can be applied by the apparatus of the present application.

Thereafter, a measurement is taken of at least one characteristic of the targeted motion segment unit as a function of the applied force (e.g. stiffness, displacement at a predetermined force and/or hysteresis). An output signal corresponding to the characteristic of the motion segment unit is then generated.

The output signal is then compared to a data bank of values of the same characteristic obtained from sample pairs of targeted adjacent vertebrae tested in the same manner as the targeted adjacent vertebrae. The values of the characteristic of the sample targeted vertebrae are matched with implantable spinal assist devices capable of reducing or eliminating instability of the targeted adjacent vertebrae.

The surgeon then selects the suitable spinal implant device, if any, and installs the same in a manner which improves stability of an otherwise unstable targeted adjacent vertebrae.

Returning to FIGS. 1–6, by reversing movement of the stepper motor 10, the pivot collar assembly 37 is forced to move downwardly, thereby causing the first segments 34a and 34b to move towards each other and thus cause the second segments 36a and 36b to likewise move toward each other and thereby relieve the force applied to the adjacent portions of the motion segment unit.

Translation of the movement of the distractor arms into a signal for determining the relative stiffness of the spine can be made in accordance with U.S. Pat. No. 4,899,761 incorporated herein by reference.

As is apparent from the description of the embodiment of the present invention provided herein, the apparatus of the present invention is designed to minimize invasion of spinal tissues and may be used by both posterior and anterior surgical procedures, including posterior lateral and anterior lateral, and lateral procedures. The apparatus provides unimpaired line of sight and provides for ready separation of the distractor arm assembly from the stepper motor assembly. The apparatus further provides an efficient, less invasive means of applying a force against targeted motion segment units to enable a surgeon to perform the diagnostic and implantation procedures described in U.S. patent application Ser. No. 10/683,505 filed on Oct. 10, 2003.

The apparatus in FIGS. 1–6 may be used as part of a system for evaluating instability of a motion segment unit as shown for example in U.S. Pat. No. 4,899,761 incorporated herein by reference. By way of example and referring to FIG. 7, the apparatus 2 of the present invention includes a distractor arm assembly 108 including a stepper motor assembly 104 which is capable of applying a force to the pair of distractor arms 32a and 32b. The stepper motor assembly is variable in both speed and torque. The torque and rotational speed produced by the motor is dependent upon the power available to the motor. Thus, the rotational speed of the motor is variable, depending on the rate at which a computer 122 sends voltage impulses via an input/output port 120 through a motor stepping circuit 122 to the stepper motor assembly 4. Each voltage pulse can be set to a constant rate of motor revolution (e.g., 1.8 degrees) so that, for instance, 200 pulses are required for each revolution of the stepper motor assembly 4.

Figure 7:
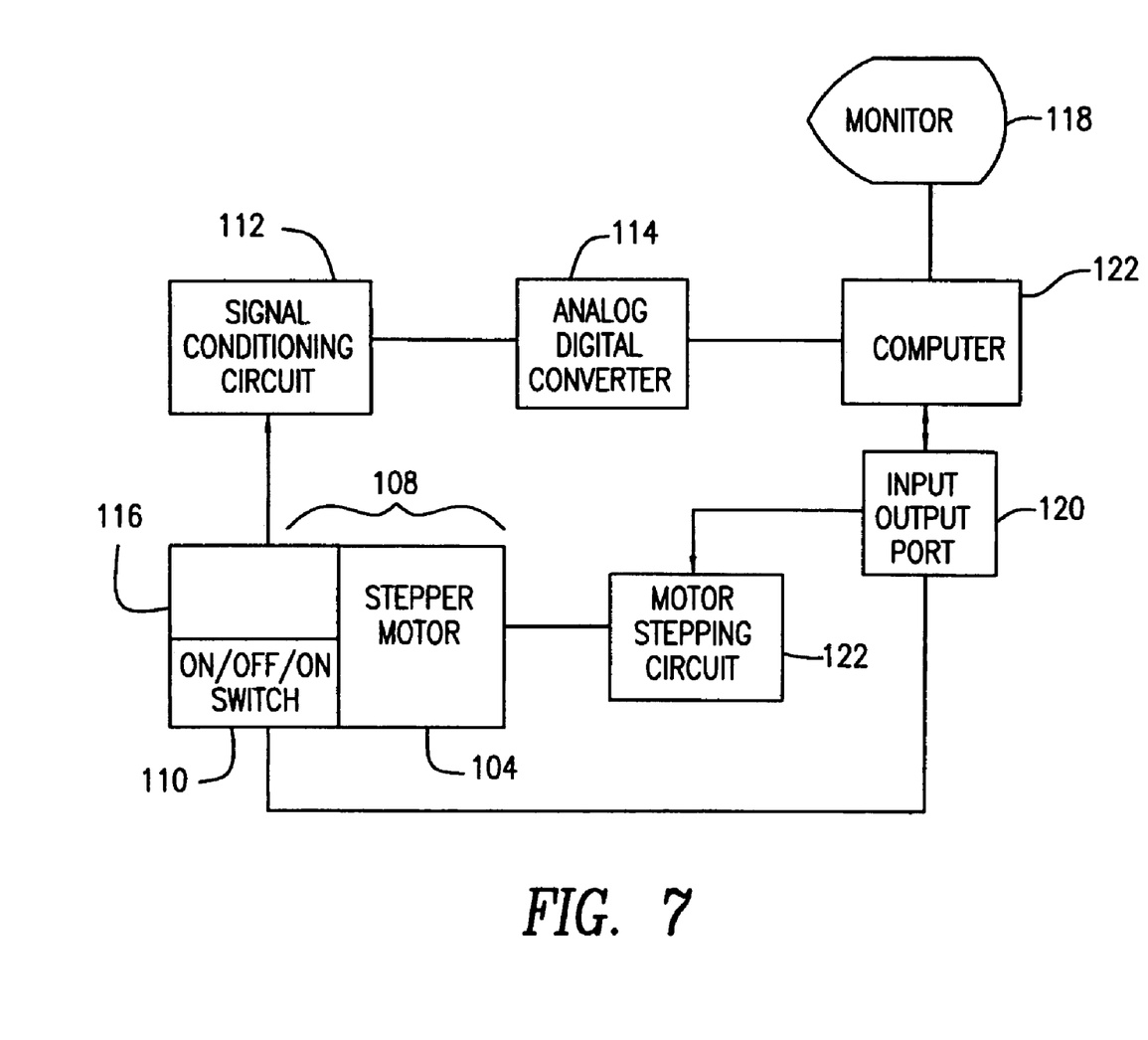
FIG. 7 is a schematic view of a system for evaluating instability of the motion segment unit using the apparatus of the present invention.

The input/output port 120 of the computer 122 sends a signal in the form of a voltage pulse (e.g., 12 volts) to the motor stepping circuit 122 to control the rate at which the stepper motor assembly 4 rotates. Each pulse is sufficient to cause the stepper motor assembly 4 to rotate at a constant rate (e.g. 1.8 degrees). A desired pulse rate has been found to be between about 30 to about 60 pulses (e.g. 40 pulses per second). If the rate of rotation is too slow, the motion segment unit will tend to "creep" or undergo additional distraction which leads to a false reading of stiffness, which is measured by dividing the resulting force by the distance of distraction.

The load cell or strain gauge 116 operates as a load transducer and detects the resistance of the adjacent vertebrae to the force being applied by the pair of distractor arms 32a and 32b, and translates the same into a voltage (in milivolts). Accordingly, the voltage produced by strain gauge 116 is a function of the resistance to the force applied, and is translated into a voltage, which is typically in the range from 0 (no load) to about 12 millivolts (maximum load). A maximum voltage of about 12 millivolts is equivalent to about 200 newtons of stress, since the voltage varies directly with the stress, since the voltage varies directly with the stress.

The load cell or strain gauge 116 transmits a signal corresponding to the change in voltage to a signal conditioning circuit 112 which has a two-fold function. First, the signal conditioning circuit 112 filters out extraneous voltage interference such as minute voltage signals emanating from fluorescent lights, etc. and, second, it amplifies the voltage signal from the strain gauges 116 from mV to V units so that the change in voltage may be read by an analog to digital converter 114. The signal conditioning circuit 112 translates the millivolt signal from the stress gauge 116 into a voltage readout of from 0–10 volts, or other suitable range as desired.

The analog to digital converter 114 converts the amplified signal from the signal condition circuit 112 into force, units, (e.g. newtons) which can be read by computer 122. For example, the converter 114 converts the voltage from the signal conditioning voltage (e.g. 0–10 volts) to a digital readout of, for example, 0 to 255 units. The computer 122 is equipped with stored data which can interpret and convert the maximum load (e.g. 200 newton load) applied to the vertebrae. The results may be viewed on a monitor 118 and compared to previously acquired data such as data acquired from motion segment units of normal subject having similar physiologic backgrounds as described in U.S. Pat. No. 10/683,505 filed on Oct. 10, 2003. As shown in FIG. 7, the apparatus of the present invention is placed into operation by placing the distractor arm assembly 108 into position between adjacent vertebrae and then activating the stepper motor assembly 104 by moving switch 110 to the "on" position. The system is deactivated by moving the switch 110 to the "off" position and removing the distractor arm assembly 108 from its position between the adjacent vertebrae. In accordance with the present invention, the system may be used in the operating room to enable the surgeon to quantitatively determine whether fusion of a motion segment unit is necessary to insure stability at the level of the spine in question, or reconstruction of a motion segment unit, or intervertebral disc replacement, or disc nucleus replacement, or ligament replacement, is necessary to insure stability at the level of the spine in question.

A method of measuring the relative stiffness of a motion segment unit as disclosed in U.S. patent application Ser. No. 10/683,505 filed on Oct. 10, 2003, incorporated herein by reference may be used with the apparatus of the present invention. The method includes applying a force against at least one pair of "targeted" adjacent vertebrae of the patient. The application of force can be applied by the apparatus of the present application.

Thereafter, a measurement is taken of at least one characteristic of the targeted motion segment unit as a function of the applied force (e.g. stiffness, displacement at a predetermined force and/or hysteresis). An output signal corresponding to the characteristic of the motion segment unit is then generated.

The output signal is then compared to a data bank of values of the same characteristic obtained from sample pairs of targeted adjacent vertebrae tested in the same manner as the targeted adjacent vertebrae. The values of the characteristic of the sample targeted vertebrae are matched with implantable spinal assist devices capable of reducing or eliminating instability of the targeted adjacent vertebrae.

The surgeons then select the suitable spinal implant device, if any, and installs the same in a manner which improves stability of an otherwise unstable targeted adjacent vertebrae.

In a further aspect of the present invention, the apparatus is provided with dual leg assemblies pivotably connected to the remote ends of the second segments.

Referring to the drawings and specifically to FIGS. 8–11, there is shown an apparatus 2 of the present invention which includes a stepper motor assembly 4 (See FIG. 6) of the type described in U.S. Pat. No. 4,899,761 incorporated herein by reference contained within a housing 6. The apparatus also includes a distractor arm assembly 8 which, as described in detail hereinafter, is able to apply a constant rate of distraction (displacement control) and/or a constant rate of force (force control) is applied, to spaced apart locations of a motion segment unit to separate the same and/or to enable the determination of reliable data on the relative stiffness, or displacement of the motion segment unit.

Rotational movement is provided through an assembly including a coupler 18 which secures a jackscrew 20 therein. A series of ball bearings 22 secures the remote end of the jackscrew to the motor housing 6. There is also provided a load cell or strain gauge 16 for measuring resistance to the force applied by the distraction arm assembly.

A collar assembly 24 is operably connected to a lower portion of the housing 6. The collar assembly 24 is secured to the housing 6 through a port 26. An opening 28 is provided within the collar assembly 24 to allow the jackscrew 20 to pass therethrough into the housing 6.

Attached to the collar assembly 24 is the distractor arm assembly 8 which in accordance with the present invention includes two segmented distractor arms 32a and 32b. Each distractor arm 32a, 32b is provided with first segments 34a and 34b, and second segments 36a and 36b, respectively. The distractor arm assembly 8 may be released from the collar assembly 24 by operation of a release means 60.

The first segments 34a and 34b are operably and rotatably connected to the collar assembly 24 through a connecting device 38a and 38b such as a screw, bolt or the like. The first segments 34 are operatively and rotatably connected to the second segments 36 through a similar type of connecting device 40a and 40b.

Figure 8:
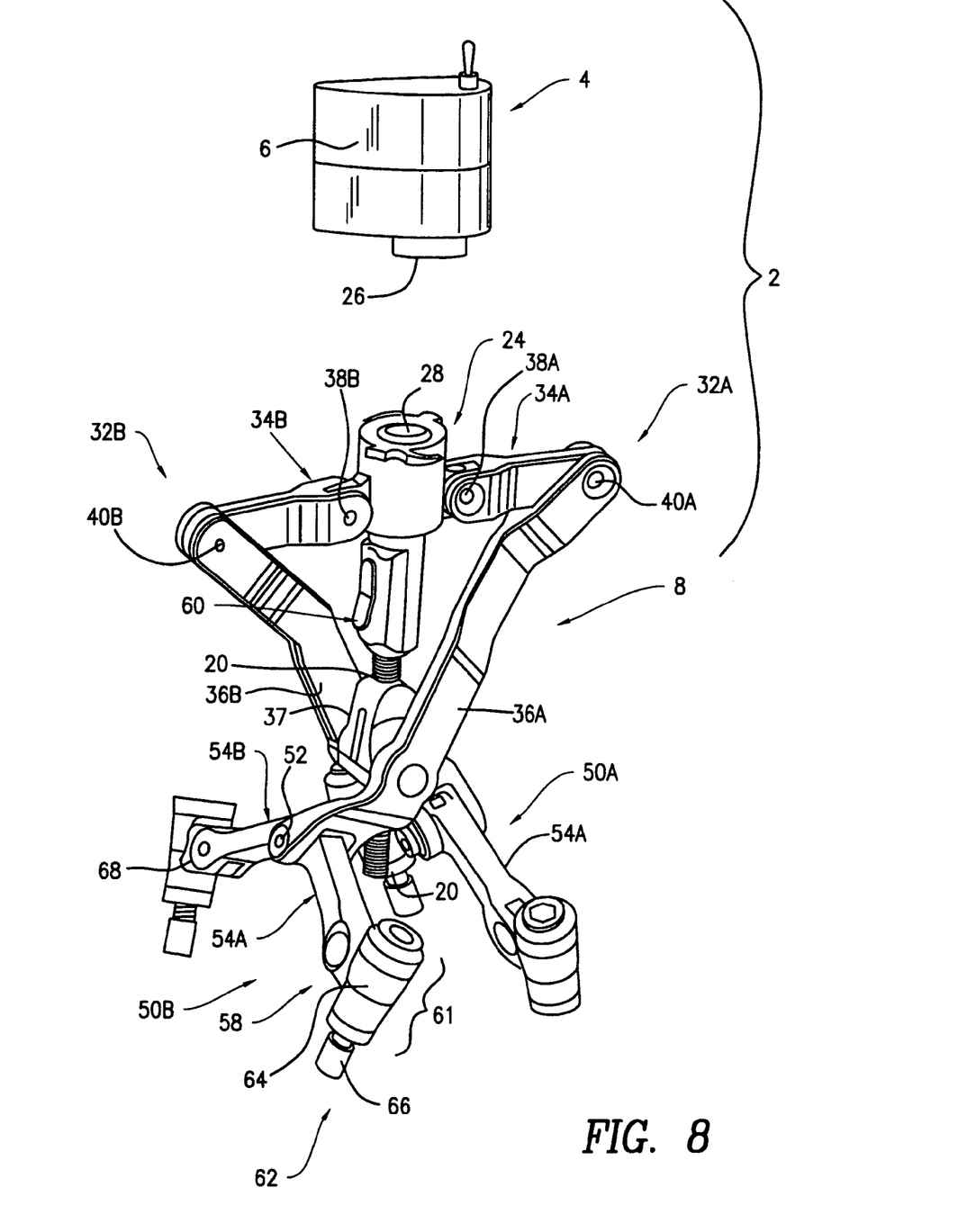
FIG. 8 is a side elevational view of a further embodiment of the apparatus of the present invention employing a distractor arm assembly including a dual leg assembly.

As shown for example in FIG. 8, the second segments 36a and 36b are linked to the jackscrew 20 through a pivot collar assembly 37. As a result, the second segments 36a and 36b are able to rotate with respect to each other thereby enabling the remote ends of the second segments to move toward and away from each other as described hereinafter.

At the remote end of the second segments 36, there is provided a motion segment unit engaging device for engaging a portion of a motion segment unit of the spine. There is provided a pair of dual leg assemblies 50a and 50b pivotally connected to the respective ends of the second segments 36a and 36b. The pivotable connection is through a connecting device 52 which may be in the form of a screw, bolt, pin or the like. The dual leg assembly 50 is comprised of a pair of legs 54a and 54b having a forward end attached via the connecting device 52 to the second segment 36a and 36b, respectively. The remote end 58 is attached to a motion segment unit engaging device 61 which may employ contact surfaces for directly engaging a portion of the motion segment unit of the spine or, as specifically shown in FIG. 8 providing a connection means 62 for engaging a pin or other device (e.g. pedicle screw and bone drill bit) which is preinserted into a portion of the motion segment unit as described hereinafter.

The connection means 62 has an upper portion 64 which rotatably engages one of the legs 54a or 54b and a lower portion 66 particularly adapted to reversibly engage the head of a preinserted pin screw (e.g. pedicle screw) or bone drill bit which has been secured within the motion segment unit of the spine as shown in FIG. 5.

The upper portion 64 may comprise a collet and bushing for securing the lower portion 66 to the corresponding leg 54a or 54b. The upper portion 64 includes a leg receiving slot 68 for securing the leg to the upper portion allowing at least some degree of rotational movement so that the motion segment unit engaging assembly 61 may be secured about the pin, screw or bone drill bit preinserted into the motion segment unit.

As specifically shown, for example, in FIG. 8, one embodiment of the invention provides for two pair of motion segment unit engaging assemblies 61 to enable interaction with spaced apart portions of the motion segment unit to provide a controllable force, sufficient for determining a characteristic (e.g. stiffness) of the motion segment unit.

Figure 9:
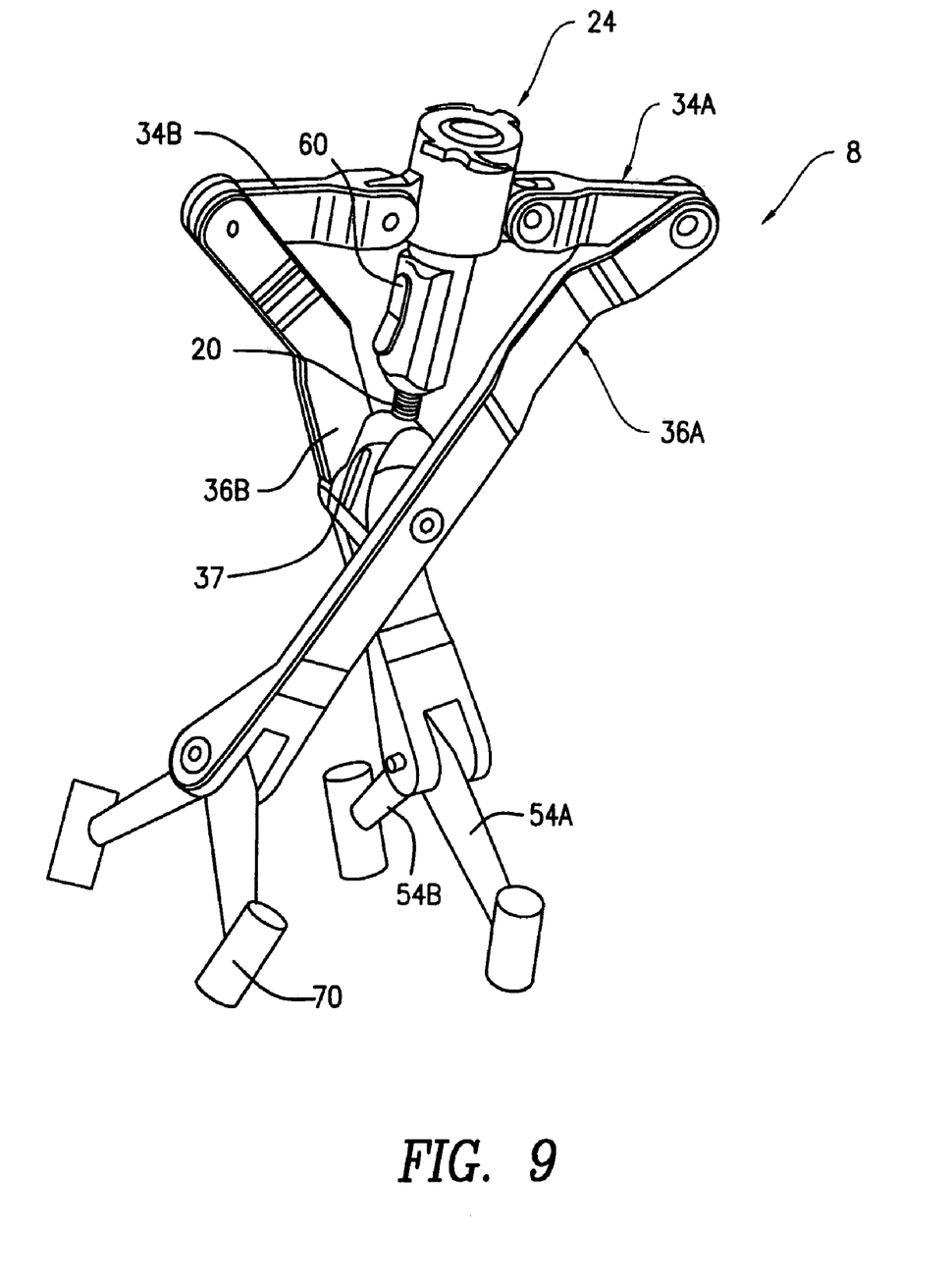
FIG. 9 is a perspective view of a further embodiment of a distractor arm assembly having a dual leg assembly in accordance with the present invention.
Figure 10:
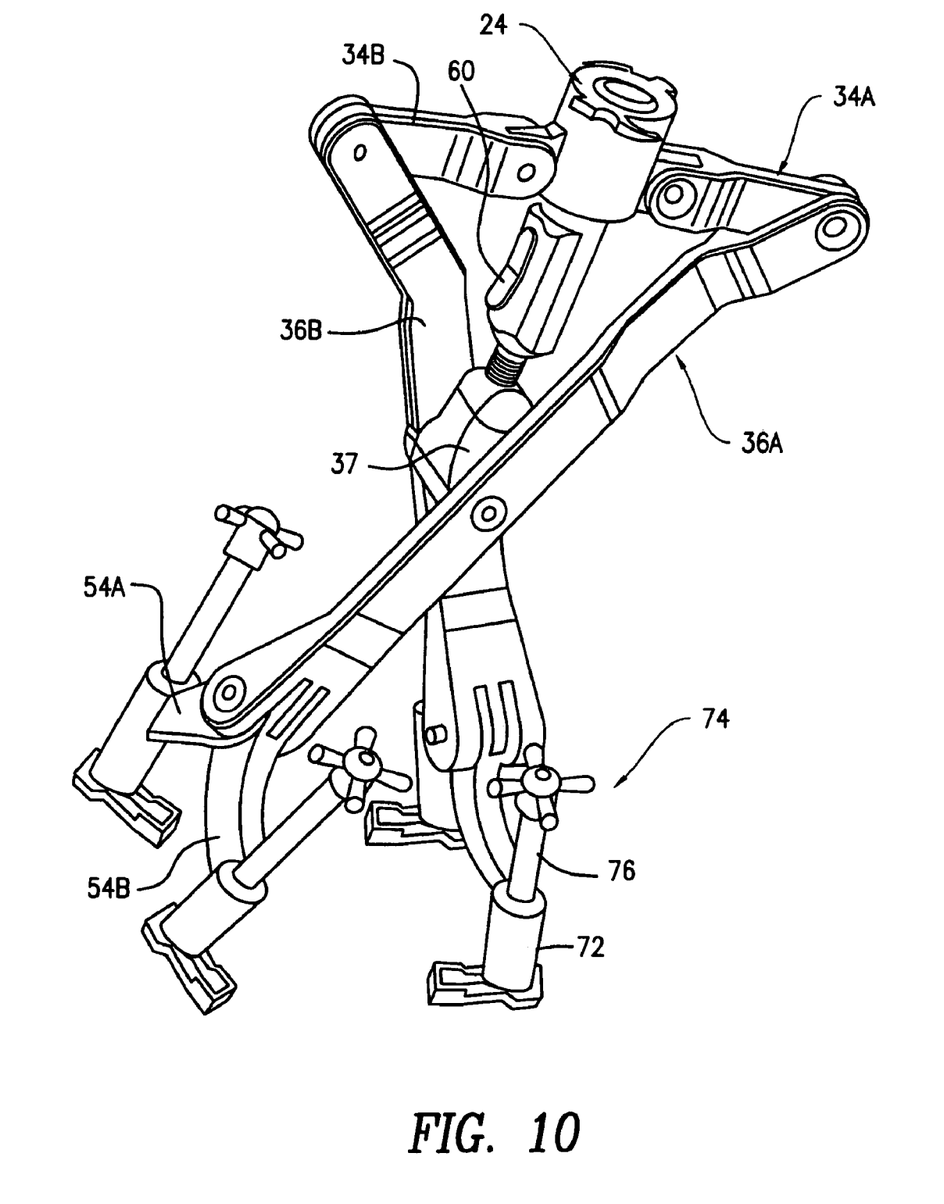
FIG. 10 is a perspective view of a further embodiment of the distractor arm assembly having a dual leg assembly in accordance with the present invention.
Figure 11:
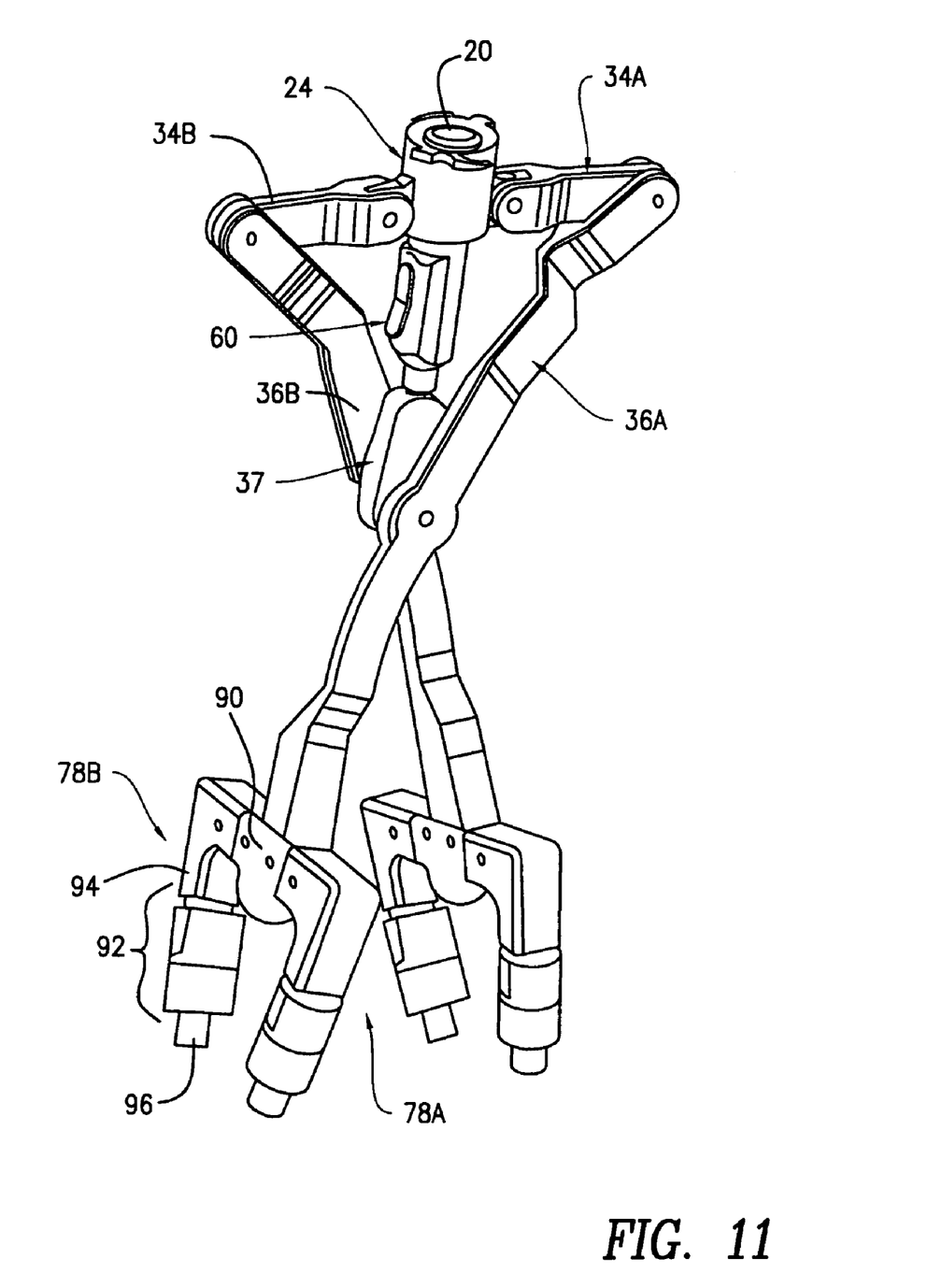
FIG. 11 is a perspective view of a still further embodiment of the distractor arm assembly having a dual leg assembly of the present invention.

Other embodiments of the dual leg assemblies are shown in FIGS. 9–11 and include different mechanisms by which the pin, pedicle screw or bone drill bit, preinserted into the motion segment unit, may be engaged by the dual leg assembly. Specifically, FIG. 9 shows a simple cylindrical tube 70 which has an interior profile adapted to engage and reversibly secure the pin, pedicle screw or bone drill bit that has been preinserted into the motion segment unit.

FIG. 10 provides for a cylindrical tube 72 which includes a knob 74 and screw down shaft 76 for reversibly securing the head of the pin, pedicle screw or bone drill bit within the dual leg assembly.

FIG. 11 is a further embodiment of the invention in which the dual leg assembly is comprised of a pair of parallel legs 78a and 78b which are essentially fixed with respect to each other by a connecting device 90. Rotational movement therefore is contained within a connection means 92 which is comprised of an upper portion 94 having attached thereto a lower portion 96 similar to that describing the embodiment of FIG. 8.

As shown in FIG. 5, the motion segment unit of a spine shown generally by the numeral 44 may be provided with a pin, pedicle screw or the like shown generally by the numeral 46 which is preinserted into the motion segment unit and has a head portion 48 which is adapted to be engaged by the dual leg assembly attached to the second segment 36 of the distractor arm assembly 8. The dual leg assembly and particularly the lower portion thereof is fitted in reversible locking engagement to the head portion 48 of the pin 46 so that the head portion 48 of the pin 46 may be inserted into the lower portion (e.g. 66 as shown in FIG. 8) of the motion segment unit engaging assembly 61 to provide reversible locking engagement with the second segment 36 of the distractor arm assembly 8.

Movement of the distractor arm assembly 8 of this embodiment is provided in a manner similar to that described for the embodiment of the present apparatus shown in FIGS. 1–7. As shown best in FIGS. 4 and 8–11, the stepper motor assembly 4 provides rotational movement to the jackscrew 20 through the drive gear 12 and idler gear 14. The jackscrew 20 is secured to the stepper motor assembly 4 through the employment of the coupler 18 and ball bearings 22. Rotational movement of the stepper motor causes the jackscrew 20 to rotate and thereby enable the pivot collar assembly 37 to move upwardly along the jackscrew towards the stepper motor assembly 4. As the pivot collar assembly 37 moves upwardly, the first segments 34a and 34b move away from each other thereby causing a similar movement in the second segments 36a and 36b thereby causing the dual leg assemblies 50a and 50b attached to the second segments 36a and 36b, respectively (see FIG. 8) to move away from each other thereby moving the respective portions of the motion segment unit away from each other.

By reversing movement of the stepper motor 10, the pivot collar assembly 37 is forced to move downwardly, thereby causing the first segments 34a and 34b to move towards each other and thus cause the second segments 36a and 36b to likewise move toward each other thereby relieving the force applied to the adjacent portions of the motion segment unit.

As with the apparatus of FIGS. 1–6, the embodiments of FIGS. 8–11 may be used as part of a system for evaluating instability of a motion segment unit as shown for example in U.S. Pat. No. 4,899,761 incorporated herein by reference as previously described.

A method of measuring a characteristic (e.g. relative stiffness) of a motion segment unit as disclosed in U.S. patent application Ser. No. 10/683,505 filed on Oct. 10, 2003 may be used with this embodiment of the present invention as previously described with respect to the embodiment of FIGS. 1–7.

What is Claimed is:

1. Apparatus for measuring instability of a motion segment unit of a spine comprising:
    a) motor means comprising a housing and a motor contained within the housing for applying a controllable force to a distractor arm assembly;
    b) a distractor arm assembly operatively engaged to the motor means comprising:
        1. a collar assembly fixedly secured to the housing of the motor means, said collar assembly having an opening to allow a screw means to pass therethrough,
        2. screw means having a first end operatively engaged to the motor means and a second end operatively engaged to a pivot collar assembly, said screw means having an unthreaded portion passing through said collar assembly and being rotatable when the motor means is operational,
        3. a pair of segmented arms each having at least two arm segments pivotal with respect to each other, a first segment being attached to the collar assembly and a second arm segment being pivotally attached to a pivot collar assembly and having a remote end for engaging a portion of the motion segment unit of the spine wherein the second arm segments transverse each other at said pivot collar assembly, and
        4. a pivot collar assembly for engaging the second arm segments enabling the second arm segments to transverse each other and be pivotally movable with respect to each other to enable the remote ends to engage and disengage the motion segment unit,
    wherein rotation of the screw means causes the pivot collar assembly to move along the screw means causing the first and second arm segments to move in said transverse relationship relative to each other whereby the remote ends of the arms move away from each other to provide a controllable force on adjacent portions of a motion segment unit and toward each other to release the controllable force against said adjacent portions.

2. The apparatus of claim 1 wherein the controllable force is a constant rate of force.

3. The apparatus of claim 1 further comprising motion segment unit contacting devices secured to the remote ends of the arms, said motion segment unit engaging devices engaging the respective portions of the motion segment units.

4. The apparatus of claim 3 wherein the motion segment unit contacting devices are selected from the group consisting of pins, pedicle screws and bone drill bits and combinations thereof.

5. The apparatus of claim 1 further comprising means for measuring resistance to the force applied by the motor means to the distractor arm assembly.

6. The apparatus of claim 5 wherein the means for measuring resistance is a load cell or strain gauge.

7. The apparatus of claim 1 wherein the motor means is a stepper motor assembly.

8. The apparatus of claim 1 wherein the screw means is a jackscrew.

9. The apparatus of claim 1 further comprising means for releasing the distractor arm assembly from the motor means.

10. The apparatus of claim 1 comprising means for rotatably connecting one of said arm segments to the collar assembly.

11. The apparatus of claim 3 wherein the motion segment unit contacting devices are inserted into the motion segment unit, said remote end of the second arm segment comprising means for reversible locking the second arm segment to the motion segment unit contacting devices.

12. The apparatus of claim 1 wherein the controllable force is sufficient to provide a constant rate of distraction on the motion segment unit.

13. The apparatus of claim 1 further comprising:
    a) detection means connected to said distractor arm assembly for measuring the resistance of the pair of arms to said distraction which is related to the resistance of the adjacent vertebrae of the motion segment unit to said distraction, at a plurality of force-exerting positions, said detection means generating an output signal corresponding to said resistance; and
    b) translation means adapted to receive said output signal from said detection means and for translating said output signal into interpretable data.

14. The apparatus of claim 1 wherein the remote ends of the second arm segments comprise a dual leg assembly comprising a pair of legs having a forward end attached to the second arm segments and a remote end comprising a motion segment unit engaging assembly.

15. The apparatus of claim 14 wherein the motion segment unit engaging assembly includes a motion segment unit contacting device.

16. The apparatus of claim 15 wherein the motion segment unit contacting devices is a pin, pedicle screw and bone drill or combination thereof.

17. A method of measuring instability of a motion segment unit of the spine comprising applying a controllable force to a distractor arm assembly operatively engaged to the motion segment unit, said distractor arm assembly comprising:
  a distractor arm assembly operatively engaged to the motor means comprising:
  1. a collar assembly fixedly secured to the housing of the motor means, said collar assembly having an opening to allow a screw means to pass therethrough.
  2. screw means having a first end operatively engaged to the motor means and a second end operatively engaged to a pivot collar assembly, said screw means having an unthreaded portion passing through said collar assembly and being rotatable when the motor means is operational,
  3. a pair of segmented arms each having at least two arm segments pivotal with respect to each other, a first segment being attached to the collar assembly and a second arm segment being pivotally attached to a pivot collar assembly and having a remote end for engaging a portion of the motion segment unit of the spine wherein the second arm segments transverse each other at said pivot collar assembly, and
  4. a pivot collar assembly for engaging the second arm segments enabling the second arm segments to transverse each other and be pivotally movable with respect to each other to enable the remote ends to engage and disengage the motion segment unit,
  wherein rotation of the screw means causes the pivot collar assembly to move along the screw means causing the first and second arm segments to move in said transverse relationship relative to each other whereby the remote ends of the arms move away from each other to provide a controllable force on adjacent portions of a motion segment unit and toward each other to release the controllable force against said adjacent portions.

18. The method of claim 17 comprising rotating the screw means causing the pivot collar assembly to move along the screw means causing the first and second arm segments to move relative to each other to provide the controllable force on adjacent portions of the motion segment unit and toward each other to release the controllable force against said adjacent portions, said controllable force generating data corresponding to a characteristic of the motion segment unit.

19. The method of claim 18 wherein the characteristic of the motion segment unit is stiffness.

* * * * *